United States Patent

White et al.

(10) Patent No.: US 7,655,821 B1
(45) Date of Patent: Feb. 2, 2010

(54) DIRECT HYDROCARBONYLATION PROCESS

(75) Inventors: Daniel F. White, West Chester, PA (US); David John Cole-Hamilton, St. Andrews (GB); Ine Boogaerts, St. Andrews (GB)

(73) Assignee: Lyondell Chemical Technology, L.P., Greenville, DE (US)

(*) Notice: Subject to any disclaimer, the term of this patent is extended or adjusted under 35 U.S.C. 154(b) by 0 days.

(21) Appl. No.: 12/313,814

(22) Filed: Nov. 25, 2008

(51) Int. Cl.
*C07C 31/18* (2006.01)
(52) U.S. Cl. .................................... 568/852
(58) Field of Classification Search .................. 568/852
See application file for complete search history.

(56) References Cited

U.S. PATENT DOCUMENTS

| 4,064,145 | A | 12/1977 | Taylor |
| 4,215,177 | A | 7/1980 | Strassel |
| 4,238,419 | A | 12/1980 | Matsumoto et al. |
| 4,306,087 | A | 12/1981 | Matsumoto et al. |
| 4,567,305 | A | 1/1986 | Matsumoto et al. |
| 4,678,857 | A | 7/1987 | Dureanleau et al. |
| 5,290,743 | A | 3/1994 | Chang |
| 5,504,261 | A | 4/1996 | Mullin et al. |
| 5,817,848 | A | 10/1998 | Kamer et al. |
| 6,127,584 | A | 10/2000 | Zajacek et al. |
| 7,271,295 | B1 | 9/2007 | White et al. |
| 7,279,606 | B1 | 10/2007 | White |

FOREIGN PATENT DOCUMENTS

| JP | S52-78809 | 7/1977 |
| JP | 06-279344 | 4/1994 |
| JP | 06-279345 | 4/1994 |

OTHER PUBLICATIONS

Casey, et al., "(Chelating diphosphine)rhodium-Catalyzed Deuterioformylation of 1-Hexene: Control of Regiochemistry by the Kinetic Ratio of Alkylrhodium Species Formed by Hydride Addition to Complexed Alkene," *Journal of American Chem. Society.*, 1995, 117, 6007-6014.
Van Der Veen, et al., "New Phosphacyclic Diphosphines for Rhodium-Catalyzed Hydroformylation," *Organometallics*, 1999, 18, 4765-4777.

*Primary Examiner*—Sikarl A Witherspoon
(74) *Attorney, Agent, or Firm*—Kevin M. Carroll

(57) ABSTRACT

A direct hydrocarbonylation process for the production of 1,4-butanediol is described. The process comprises reacting allyl alcohol with carbon monoxide and hydrogen in an alcohol solvent in the presence of a catalyst system comprising a rhodium complex, a trialkyl phosphine, and a diphosphine. The process gives a high yield of 1,4-butanediol in a one-step reaction.

10 Claims, No Drawings

DIRECT HYDROCARBONYLATION PROCESS

FIELD OF THE INVENTION

This invention relates to a process for hydrocarbonylating allyl alcohol to produce 1,4-butanediol.

BACKGROUND OF THE INVENTION

The production of 1,4-butanediol from allyl alcohol is a well-known and commercially practiced process. See, for example, U.S. Pat. Nos. 4,238,419, 4,678,857, 4,215,177, 5,290,743 and the like. Generally, the process consists of a hydroformylation reaction followed by hydrogenation step. In hydroformylation, allyl alcohol is reacted with a $CO/H_2$ gas mixture using a rhodium-phosphine catalyst system to form 4-hydroxybutyraldehyde (HBA), with some 3-hydroxy-2-methylpropionaldehyde (HMPA). Then, the HBA is typically separated from the catalyst by water extraction and hydrogenated over a nickel catalyst to form 1,4-butanediol. See U.S. Pat. No. 5,504,261.

The above reaction sequence involves the use of different catalysts and usually different reaction gas mixtures for each of the reactions. For the hydroformylation reaction, most notably a rhodium complex is used together with a phosphine ligand (see, e.g., U.S. Pat. Nos. 4,064,145, 4,238,419, and 4,567,305). Commonly employed phosphine ligands are trisubstituted phosphines such as triphenyl phosphine. U.S. Pat. No. 6,127,584 discloses the use of a trialkyl phosphine ligand having at least 2 methyl groups. The use of diphosphine ligands such as DIOP, trans-1,2-bis(diphenyl-phosphinomethyl)cyclobutane, trans-1,2-bis(bis(3,5-di-n-alkylphenyl)-phosphinomethyl)cyclobutane, and 2,3-o-isopropylidene-2,3-dihydroxy-1,4-bis[bis(3,5-di-n-alkylphenyl)phosphino]butane is also taught in the art, notably in Japan Kokai Nos. 06-279345 and 06-279344 and U.S. Pat. Nos. 4,306,087, 7,271,295, and 7,279,606.

Direct hydrocarbonylation reactions of allyl alcohol to produce 1,4-butanediol have also been taught in the art. It has been reported, for example, in Kokai No. S52-78809 by Kawahito, et al. that 1,4-butanediol can be produced from allyl alcohol in a one-step reaction using a rhodium and a trialkyl phosphine catalyst system. However, these processes typically result in a relatively low ratio of 1,4-butanediol to 2-methyl-1,3-propanediol and also produce a significant amount of less valuable isobutanol by-product. U.S. Pat. No. 6,127,584 discloses a two-step, one catalyst process using rhodium and a trialkyl phosphine wherein higher ratios of 1,4-butanediol to 2-methyl-1,3-propanediol are produced.

In sum, new processes for the direct hydrocarbonylation of allyl alcohol to produce 1,4-butanediol in a single step are needed.

SUMMARY OF THE INVENTION

The invention is a process that comprises reacting allyl alcohol with carbon monoxide and hydrogen in an alcohol solvent and in the presence of a catalyst system to produce 1,4-butanediol. The catalyst system comprises a rhodium complex, a trialkyl phosphine, and a diphosphine ligand.

DETAILED DESCRIPTION OF THE INVENTION

The process of the invention comprises hydrocarbonylating allyl alcohol in the presence of an alcohol solvent and a catalyst system. The catalyst system comprises a rhodium complex, a trialkyl phoshine ligand, and a bidentate diphosphine ligand.

Diphosphine ligands contain two phosphine atoms that are covalently bonded to one another through a bridging group that contains at least one nonhydrogen atom. Diphosphine ligands are well known in the art. Examples of suitable diphosphine ligands include DIOP [2,3-O-isopropylidene-2,3-dihydroxy-1,4-bis(diphenylphosphino)butane], XANTPHOS [4a,9a-dihydro-9,9-dimethyl-4,5-bis(diphenylphosphino)xanthene], DIPHOS [1,2-bis(diphenylphospino)-ethane], BISBI [2,2'-bis(diphenylphospino)methyl-1,1'-biphenyl], T-BDCP [trans-1,2-bis((diphenylphospino)methyl)cyclopropane], and CHDIOP (see, for example, Casey, et al., *J. Am. Chem. Soc.*, 1995, 117, 6007, van der Veen, et al., *Organometallics*, 1999, 18, 4765, and U.S. Pat. No. 5,817,848). Examples also include trans-1,2-bis(bis(3,5-di-n-alkylphenyl)phosphino-methyl)cyclobutane taught in U.S. Pat. Nos. 7,279,606 and 2,3-O-isopropylidene-2,3-dihydroxy-1,4-bis[bis(3,5-di-n-alkylphenyl)phosphino]butane taught in U.S. Pat. No. 7,271,295.

Preferred diphosphine ligands include those diphosphine ligands in which the phosphine atoms are covalently bonded to one another through a $C_4$ bridging group, such as DIOP, trans-1,2-bis(bis(3,5-di-n-alkylphenyl)-phosphinomethyl) cyclobutane, and 2,3-O-isopropylidene-2,3-dihydroxy-1,4-bis[bis(3,5-di-n-alkylphenyl)phosphino]-butane.

Preferred trans-1,2-bis(bis(3,5-di-n-alkylphenyl)phosphinomethyl)-cyclobutane ligands include trans-1,2-bis(bis(3,5-dimethylphenyl)-phosphinomethyl)cyclobutane (DXPM-CyB) and trans-1,2-bis(bis(3,5-diethylphenyl) phosphinomethyl)cyclobutane.

Preferred 2,3-O-isopropylidene-2,3-dihydroxy-1,4-bis[bis(3,5-di-n-alkyl-phenyl)phosphino]butanes include 2,3-O-isopropylidene-2,3-dihydroxy-1,4-bis[bis(3,5-dimethylphenyl)phosphino]butane and 2,3-O-isopropylidene-2,3-dihydroxy-1,4-bis[bis(3,5-diethylphenyl)phosphino]butane.

The trialkyl phosphine ligand is a trisubstituted phosphine that is represented by the formula:

$$(R^1)_3P$$

wherein $R^1$ is an alkyl group. Suitable aliphatic $R^1$ groups include methyl, ethyl, propyl, butyl, hexyl, octyl, and decyl. Preferably, the $R^1$ groups are methyl, ethyl, n-propyl, or n-butyl. The $R^1$ groups may be the same or are different, but preferably are the same. Preferably, the trialkyl phosphine is trimethyl phosphine, triethyl phosphine, tri-n-propyl phosphine, tri-n-butyl phosphine, or mixtures thereof.

The catalyst system also comprises a rhodium complex. Suitable rhodium complexes contain rhodium attached to ligand groups. The rhodium complex is preferably soluble in the solvent. There are no particular restrictions regarding the choice of ligands attached to the rhodium complex. For example, suitable ligands include hydrides, carbonyl, substituted and unsubstituted cyclopentadienyls, 2,4-alkanedionates, trialkyl or triaryl phosphines, diphosphines, and mixtures thereof. Particularly preferred ligands include carbonyl, acetylacetonate (2,4-pentanedionate), triphenylphosphine, and mixtures thereof. Examples of preferred rhodium complexes include (acetylacetonato) dicarbonylrhodium and tris(triphenylphosphine)rhodium carbonyl hydride.

The rhodium complex can be pre-associated with the diphosphine ligand and the trialkyl phosphine ligand prior to use in the hydrocarbonylation reaction such that the diphosphine and trialkyl phosphine ligands form part of the rhodium complex, or it can be added separately. However, it is preferable to add the rhodium complex separate from the diphosphine and trialkyl phosphine ligands. The molar ratio of the diphosphine:rhodium complex is preferably in the range of 0.5:1 to 10:1, more preferably 1:1 to 5:1. The molar ratio of trialkyl phosphine:rhodium complex is preferably in the range of 0.5:1 to 10:1, more preferably 1:1 to 5:1.

An alcohol reaction solvent is also required for the process of the invention. Typical alcohol solvents are those that are capable of solubilizing the rhodium complex. Preferred alcohol solvents include $C_1$-$C_{12}$ aliphatic alcohols and $C_6$-$C_{12}$ aromatic alcohols; $C_1$-$C_4$ aliphatic alcohols are more preferred. Particularly preferred alcohol solvents include methanol, ethanol, isopropanol, t-butanol, and mixtures thereof.

Typical reaction conditions for the hydrocarbonylation reaction favor the formation of the linear 1,4-butanediol (BDO) rather than branched 2-methyl-1,3-propanediol (MPD) reaction product. Reaction temperatures are preferably in the range of from about 20 to 160° C., more preferably from about 70 to 140° C., and most preferably from about 90 to 130° C. Reaction pressures are preferably above 20 psig, more preferably from 50 to 1000 psig, and most preferably from 200 to 600 psig. Preferably, the reaction is performed at a temperature within the range of about 70° C. to about 140° C. and a pressure within the range of about 50 to about 1000 psig, and more preferably at a temperature within the range of about 90° C. to about 130° C. and a pressure within the range of about 200 to about 600 psig.

The molar ratio of $H_2$:CO is preferably 1:1 or greater, more preferably 2:1 or greater, and most preferably from about 2:1 to 5:1. The partial pressure of CO is typically within the range of 125 to 550 psig. The partial pressure of hydrogen is typically within the range of 40 to 300 psig. The reaction is typically conducted at these conditions until a predominance of the allyl alcohol has reacted, e.g. 60 to 99.9%, the products being largely 1,4-butanediol and 2-methyl-1,3-propanediol. The amount of reaction time is not critical, but usually a reaction time of 0.5 to 4 hours is adequate.

Preferably, the allyl alcohol starting concentration on a reaction solvent to feed basis is in the range of about 5 to 40 percent by weight in the solvent; more preferably, a lower concentration in the range of 5 to 10 percent by weight may be used.

During the hydrocarbonylation reaction, BDO and MPD are formed along with other low value co-product/byproducts. The process of the invention typically produces a high ratio of linear to branched alcohol products, i.e., a BDO:MPD ratio of greater than 4 is typical.

In an illustrative embodiment of the invention, allyl alcohol, an alcohol solvent such as ethanol, and the catalyst system are charged to a reactor to which is introduced the CO/$H_2$ reaction gas mixture. The reactor is heated to reaction temperature and pressurized with the CO/$H_2$ mixture for the desired reaction time to form 1,4-butanediol with high selectivity. Preferably, agitation is provided.

The product of this reaction typically contains BDO, MPD (BDO:MPD$\geq$4), some $C_4$ aldehydes (HBA and HMPA), 2-hydroxy-tetrahydrofuran (an isomer of HMPA), and $C_3$ products (n-propanol and propionaldehyde). Depending on reaction conditions, some ethoxy analogs of these product may also be present, e.g. 2-ethoxy-tetrahydrofuran.

The following examples merely illustrate the invention. Those skilled in the art will recognize many variations that are within the spirit of the invention and scope of the claims.

EXAMPLE 1

Direct Hydrocarbonylation of Allyl Alcohol

Allyl alcohol is hydrocarbonylated according to the following procedure:

A solution of diphosphine (16 mmol) and triethylphosphine (16 mmol) in dry degassed solvent (4 mL) is added under a stream of argon or nitrogen to [Rh(CO)$_2$(acac)] (8 mmol) under an argon atmosphere. The resulting solution is transferred in a gastight syringe to a 25-mL autoclave under an argon atmosphere. The autoclave is flushed twice with a 1:1 CO/$H_2$ mixture and then pressurized to 30 bar with the CO/$H_2$ mixture. The autoclave is then heated to 120° C. with stirring, the pressure is increased to 39.5 bars, allyl alcohol (1 mL) is then injected from a sidearm, and the autoclave pressurized to 40 bar with the CO/$H_2$ mixture. The autoclave is kept at a constant pressure of 40 bar, and the gas uptake of the reaction is monitored in a ballast vessel from which the gas is delivered. When there is no further gas uptake, the autoclave is cooled and depressurized. The resulting solution is analyzed by gas chromatography to determine the products of the reaction. The reaction produces BDO, MPDiol, HBA, HMPA, and $C_3$ products (n-propanol and propionaldehyde). The BDO-MPDiol selectivity (i.e., moles BDO+MPDiol produced/moles allyl alcohol converted*100%) and the ratio of BDO:MPDiol (l:b or linear:branched) is also measured.

The results, shown in Table 1, demonstrate that the use of an alcohol solvent results in much higher BDO-MPDiol selectivity and the use of a diphosphine and trialkylphosphine unexpectedly results in significantly higher BDO:MPDiol (l:b) ratio than just using a trialkylphosphine.

EXAMPLE 2

Direct Hydrocarbonylation of Allyl Alcohol at Varying Diphosphine:Phosphine Ratios The procedure of Example 1 is repeated with the exception that the diphosphine ligand used is DIOP, the solvent is ethanol, and the amounts of diphosphine ligand and triethylphosphine are varied as shown in Table 2. The example using a 1:1 diphosphine:triethylphosphine molar ratio is Example 1E from Table 1.

The results, shown in Table 2, show that all of the examples result in high BDO:MPDiol ratio, but the highest BDO-MPDiol selectivity occurs using a diphosphine:trialkylphosphine molar ratio of about 0.5 to about 2.

EXAMPLE 3

Direct Hydrocarbonylation of Allyl Alcohol at Varying Pressure and $H_2$:CO Ratios The procedure of Example 1 is repeated with the exception that the solvent is ethanol, the diphosphine ligand is XANPHOS (16 mmol), and 10 mmol of triethylphosphine is used. The reaction pressure and $H_2$:CO ratios are varied as shown in Table 3.

The results, shown in Table 3, show that a 2:1 $H_2$:CO ratio results in slightly higher productivity than 1:1 ratio.

TABLE 1

Direct Hydrocarbonylation of Allyl Alcohol

| Example | Diphosphine | Phosphine | Solvent | BDO-MPDiol Selectivity | l:b ratio |
|---|---|---|---|---|---|
| 1A* | — | PEt$_3$ | EtOH | 98.6 | 1.9 |
| 1B | Xantphos | PEt$_3$ | EtOH | 77.8 | 5.2 |
| 1C | DXPMCyB | PEt$_3$ | EtOH | 75.6 | 14.2 |
| 1D | BISBI | PEt$_3$ | EtOH | 65.5 | 4.5 |
| 1E | DIOP | PEt$_3$ | EtOH | 83.0 | 6.5 |
| 1F* | DIOP | PEt$_3$ | Toluene | 2.5 | 0.8 |

*Comparative Example

TABLE 2

Ratio of Diphosphine:Phosphine

| Example | [DIOP] mmol/L | [PEt$_3$] mmol/L | DIOP:PEt$_3$ Molar Ratio | BDO-MPDiol Selectivity | l:b ratio |
|---|---|---|---|---|---|
| 2A | 16 | 4 | 4 | 17.1 | 6.5 |
| 2B | 16 | 10 | 1.6 | 77.8 | 6.5 |
| 1E | 16 | 16 | 1 | 83.0 | 6.5 |
| 2C | 16 | 24 | 0.67 | 72.8 | 6.1 |
| 2D | 16 | 32 | 0.5 | 64.1 | 6.0 |

TABLE 3

Effect of Pressure and H$_2$:CO Ratio

| Example | Pressure (Bar) | H$_2$:CO Ratio | BDO-MPDiol Selectivity | l:b ratio |
|---|---|---|---|---|
| 3A | 60 | 1:1 | 67.4 | 4.8 |
| 3B | 60 | 2:1 | 71.9 | 4.8 |
| 3C | 40 | 1:1 | 72.1 | 5.3 |
| 3D | 40 | 2:1 | 76.5 | 5.3 |
| 3E | 20 | 1:1 | 78.1 | 5.4 |
| 3F | 20 | 2:1 | 82.6 | 5.5 |

We claim:

1. A process to produce 1,4-butanediol, comprising reacting allyl alcohol with carbon monoxide and hydrogen in an alcohol solvent in the presence of a catalyst system comprising a rhodium complex, a trialkyl phosphine ligand, and a diphosphine ligand, wherein the molar ratio of diphosphine:trialkyl phosphine is about 0.5 to about 2.

2. The process of claim 1 wherein the trialkyl phosphine ligand is selected from the group consisting of trimethyl phosphine, triethyl phosphine, tri-n-propyl phosphine, tri-n-butyl phosphine, and mixtures thereof.

3. The process of claim 1 wherein the diphosphine ligand is a trans-1,2-bis(bis(3,5-di-n-alkylphenyl)phosphinomethyl)cyclobutane.

4. The process of claim 1 wherein the diphosphine ligand is a 2,3-O-isopropylidene-2,3-dihydroxy-1,4-bis[bis(3,5-di-n-alkylphenyl)phosphino]butane.

5. The process of claim 1 wherein the diphosphine ligand is DIOP.

6. The process of claim 1 wherein the alcohol solvent is a C$_1$-C$_4$ aliphatic alcohol.

7. The process of claim 1 wherein the rhodium complex comprises rhodium and ligands selected from the group consisting of hydride, carbonyl, trialkyl or triaryl phosphines, diphosphines, cyclopentadienyls, 2,4-alkanedionates, and mixtures thereof.

8. The process of claim 1 wherein the reaction is performed at a temperature within the range of about 70° C. to about 140° C. and a pressure within the range of about 50 to about 1000 psig.

9. The process of claim 1 wherein the reaction is performed at a temperature within the range of about 90° C. to about 130° C. and a pressure within the range of about 200 to about 600 psig.

10. The process of claim 1 wherein the molar ratio of hydrogen to carbon monoxide is 2:1 or greater.

* * * * *